United States Patent [19]

Kurland

[11] Patent Number: 4,713,075
[45] Date of Patent: Dec. 15, 1987

[54] METHOD FOR THE REPAIR OF CONNECTIVE TISSUE

[76] Inventor: Kenneth Z. Kurland, 2 W. McCabe Rd., El Centro, Calif. 92243

[21] Appl. No.: 920,408

[22] Filed: Oct. 20, 1986

Related U.S. Application Data

[60] Division of Ser. No. 589,713, Mar. 15, 1984, abandoned, which is a continuation-in-part of Ser. No. 524,351, Aug. 18, 1983, Pat. No. 4,585,458, which is a continuation-in-part of Ser. No. 272,134, Jun. 10, 1981, Pat. No. 4,400,833.

[51] Int. Cl.⁴ ............................................. A61F 2/08
[52] U.S. Cl. ..................................... 623/13; 623/16; 128/335.5
[58] Field of Search ........................... 623/13, 16, 18; 128/334 R, 335.5

[56] References Cited

U.S. PATENT DOCUMENTS

| | | | |
|---|---|---|---|
| 3,805,300 | 4/1974 | Tascon-Alonso et al. | 623/13 |
| 4,329,743 | 5/1982 | Alexander et al. | 623/13 |
| 4,643,734 | 2/1987 | Lin | 623/16 |

Primary Examiner—Ronald L. Frinks
Attorney, Agent, or Firm—Charmasson & Holz

[57] ABSTRACT

A prosthetic device for repairing or replacing connective tissue such as ligaments and tendons in the human or animal body is described. The device comprises a cord of artificial connective tissue formed from a composite, partly absorbable thread. The thread comprises a combination of permanent material and absorbable material susceptible to being dissolved into surrounding living tissue. The dissolving of the absorbable material leaves space for the living tissue to grow into and adhere to the structure formed by the permanent material.

3 Claims, 5 Drawing Figures

METHOD FOR THE REPAIR OF CONNECTIVE TISSUE

PRIOR APPLICATION

This is a division of application Ser. No. 589,713 filed on Mar. 15, 1984, now abandoned, which in turn was a continuation-in-part of application Ser. No. 524,351 filed on Aug. 18, 1983, now U.S. Pat. No. 4,585,458, which in turn was a continuation-in-part of application Ser. No. 272,134 filed on June 10, 1981, and now U.S. Pat. No. 4,400,833.

BACKGROUND OF THE INVENTION

This invention is in the field of prosthetics and relates to the replacement of connective tissue structures such as ligaments and tendons with prosthetic implants.

One of the most challenging problems encountered in the use of artificial ligaments or tendons to repair or replace existing ones in humans or in animals, is that of ensuring a rapid, strong and durable bonding of the prosthesis to the host's tissues.

SUMMARY OF THE INVENTION

It is an object of the present invention to provide a prosthetic device for repairing ligaments or tendons which encourages bonding to surrounding living tissue and provides a scaffolding around which a new ligament or tendon can form. This process usually takes about two or three weeks.

According to the present invention a prosthetic device is provided which comprises a cord of artificial connective tissue formed with a composite, partly absorbable thread. The thread is formed from a combination of permanent material and absorbable material susceptible to being dissolved into surrounding living tissues.

The thread may comprise an inner core of permanent material and an outer layer of absorbable material. Alternatively, the thread is of absorbable material with wires of permanent material embedded in it.

The cord may be formed from intertwined or twisted lengths of the thread. Alternatively, the thread may be braided into a rope, the rope then being twisted or intertwined to form a cord of suitable dimensions for artificial connective tissue. In another embodiment, the cord is formed from a single length of thread of suitable dimensions. In this case, the thread preferably comprises absorbable material with wires of permanent material, suitably Dacron, embedded in it.

The cord may be cut to a desired length and is adapted to be attached as artificial connective tissue to a bone, muscle, or end of an existing length of connective tissue. The ends of the cord may each have a cap or sleeve of woven mesh fastened to them, or the cord may be completely enclosed in a woven mesh sleeve. The mesh may be woven from Dacron thread of from the composite thread. The end of each cap or sleeve is stitched to the cord using the composite thread. In another embodiment, the cord may be comprised entirely of multiple strands of composite thread and attached by tying off with sutures or other attachments of choice (e.g. staples). The composite thread is preferably also used to secure the ends of the cord to the adjacent living tissue.

Over a period of time the absorbable material of the thread in the cord and sutures will be absorbed, and new tissue or bone will grow among the fibers of the mesh caps and into the grooves in the core of each thread. This provides a strong and secure artificial ligament or tendon connection, and provides a scaffolding around which a new ligament or tendon can form.

DETAILED DESCRIPTION OF THE PREFERRED EMBODIMENT

Figure 1:
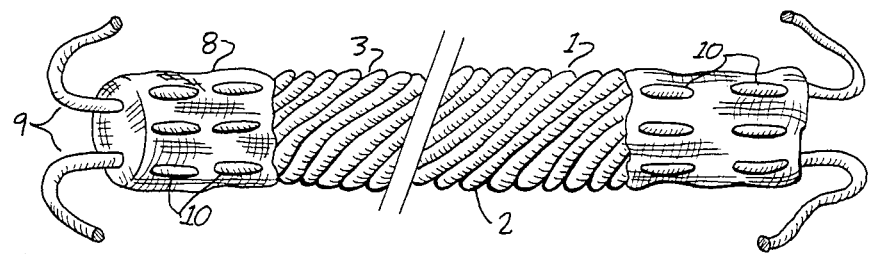
FIG. 1 shows a length of artificial connective tissue according to an embodiment of the invention.

FIG. 1 illustrates a length of artificial connective tissue according to a preferred embodiment of the invention. The connective tissue may be used to repair or replace a length of tendon or ligament in the human or animal body.

Figure 2:
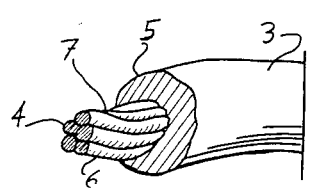
FIG. 2 shows the thread used in the artificial connective tissue of FIG. 1.

The artificial connective tissue shown in FIG. 1 comprises a cord 1 formed from lengths 2 of a composite, partly absorbable thread 3 which is illustrated in more detail in FIG. 2. Lengths of the thread 3 are intertwined, or twisted to form the cord 1 as shown in FIG. 1. The cord 1 is of suitable dimensions for artificial connective tissue.

FIG. 2 shows the thread 3 used to form the cord 1. The thread 3 comprises an inner core 4 of permanent material such as Dacron or carbon fiber, surrounded by an outer layer or coating 5 of absorbable material such as polylactic acid polymer, polyglycolic acid, polygalactin, or other material commonly used in the manufacture of absorbable sutures. The core 4 is made from several filaments 6 braided together to define serpentine grooves 7. In an alternative version (not shown) the core 4 comprises a single filament with its outer surface striated with a series of parallel serpentine grooves. Alternatively, the thread 3 may comprise absorbable material with wires of permanent material embedded in it.

As mentioned above, the cord 1 is formed of suitable diameter for a length of artificial connective tissue, for example to replace or repair a ligament or tendon. The cord 1 may be formed in lengths which are then cut to the desired size. One or each end of the cord 1 may have an end cap or sleeve 8 fastened to it as shown in FIG. 1. Alternatively one or each end may be tied off or ligated with a length of the composite thread 3, or may be fastened in any other suitable way, for example with staples.

Caps or sleeves 8 shown in FIG. 1 are formed from mesh material woven from a synthetic thread, such as Dacron or from composites of partly absorbable thread. Sutures 9 extend from each end of the cord 1. In FIG. 1, the caps or sleeves 8 are attached to the cord 1 by rows of stitches 10. Sutures 9 and stitches 10 both preferably comprise composite thread of the type shown in FIG. 2.

Figure 3:
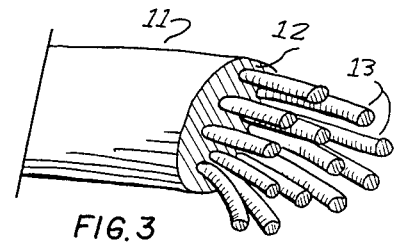
FIG. 3 shows an alternative embodiment of artificial connective tissue according to the invention.

FIG. 3 shows another embodiment of the invention where a length of artificial connective tissue is formed as a cord 11 comprising a single length of composite thread of suitable dimensions. The thread is formed from absorbable material 12 having wires 13 of permanent material suitably Dacron, embedded in it. The absorbable material 12 is the same as in the first embodiment.

Figure 4:
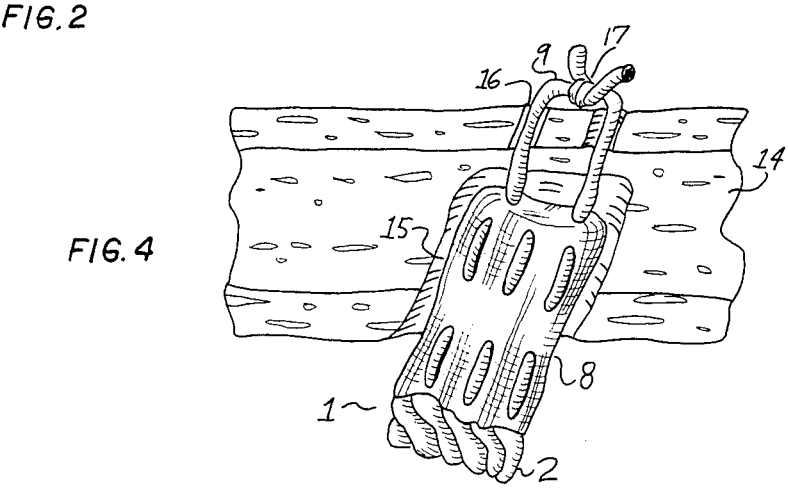
FIG. 4 illustrates the connection of one end of the artificial connective tissue of FIG. 1 to a bone.

FIG. 4 illustrates an example of the use of a cord 1 of the first embodiment as an artificial ligament connected to a bone 14. A tunnel 15 is formed in the bone 14 with a surgical drill. One end of the cord or artificial ligament 1 is inserted into the tunnel 15, and the sutures 9 are drawn through small suture holes 16 and tied off at 17. Alternatively the artificial ligament 1 may be attached via a window cut into the bone with an osteotome.

Over a time the tunnel 15 will fill in with new bone growth, and will grow interstitially between the fibers of the mesh cap 8. As the outer layer of the thread 2 from which the cord and sutures are formed is absorbed, the grooves or striations of the inner core of the threads help to anchor the cap, sutures and cord end to the surrounding tissue or bone. Thus a strong and secure connection is formed.

Figure 5:
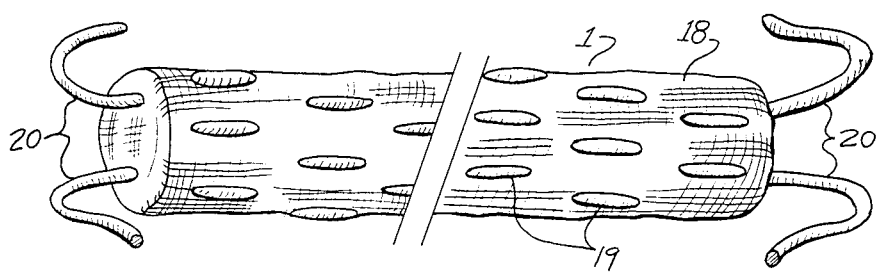
FIG. 5 shows a further embodiment of artificial connective tissue according to the invention.

FIG. 5 illustrates a modification of the embodiment of FIG. 1. In FIG. 5 the cord 1 is entirely covered by a sleeve 18 of mesh material, rather than by end caps 8 only. The mesh material is of woven synthetic material, such as Dacron or of woven composite thread. The sleeve 18 is secured to the cord 1 along its length by stitches 19 of composite thread. Sutures 20 of composite thread are provided at each end of the cord 1.

The cord of any of the above embodiments can be used as an implant to replace or repair a damaged length of tendon or ligament, and in connection with the connective tissue replacement procedures disclosed in the parent applications. it can be attached to bone or muscle at each end as shown in FIG. 4. It may be attached end to end at one or both ends to portions of existing tendon or ligament by wrapping a sleeve of mesh material around the adjacent ends and stitching the sleeve to the cord and existing ligament or tendon. The mesh material may again be woven from a synthetic thread such as Dacron, or from composite thread of the type shown in FIG. 2.

The absorbable material of the artificial ligament will be absorbed and replaced by living tissue over a period of two to three weeks. The permanent material in the ligament or tendon thus acts as a scaffolding around which a new ligament or tendon will form.

While a preferred embodiment of the invention has been described, other embodiments may be devised without departing from the spirit and scope of the appended claims.

What is claimed is:

1. A method for repairing a connective tissue lesion such as a tendon, linear ligament or capsular ligament, and for promoting the regrowth of at least one damaged portion of the tissue toward its point of attachment, which comprises:
   attaching to said portion one of each end of a plurality of lengths of composite thread comprising a core of filament coated with an absorbable composition;
   said core filaments being braided together;
   and said plurality of composite threads being braided together into a length of rope;
   tauntly securing the other ends of thread to said point of attachment; and
   allowing growth of the tissue around the lengths of thread.

2. The method of claim 1, wherein the step of attaching said one of each end to said point of attachment comprises:
   capping said ends with a mesh made of woven composite suture coated with an absorbable composition;
   drilling into a bone a bore commensurate with said capped ends; and
   tieing said capped ends into said bone.

3. The method of claim 1, wherein the step of attaching comprises braiding each of said composite thread with a plurality of lengths of sutures coated with an absorbable composition.

* * * * *